(12) United States Patent
Tamamori et al.

(10) Patent No.: US 9,696,539 B2
(45) Date of Patent: Jul. 4, 2017

(54) DEFORMABLE MIRROR AND METHOD FOR MANUFACTURING THE SAME

(71) Applicant: CANON KABUSHIKI KAISHA, Tokyo (JP)

(72) Inventors: Kenji Tamamori, Ebina (JP); Yasuhiro Shimada, Sagamihara (JP); Fumiaki Mizutani, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/180,889

(22) Filed: Feb. 14, 2014

(65) Prior Publication Data
US 2014/0232984 A1 Aug. 21, 2014

(30) Foreign Application Priority Data

Feb. 18, 2013 (JP) .................................. 2013-029355
Jan. 31, 2014 (JP) .................................. 2014-016379

(51) Int. Cl.
*G02B 26/08* (2006.01)
*A61B 3/14* (2006.01)

(52) U.S. Cl.
CPC ............ *G02B 26/0825* (2013.01); *A61B 3/14* (2013.01); *G02B 26/0841* (2013.01); *Y10T 29/49002* (2015.01)

(58) Field of Classification Search
CPC ............ G02B 26/0825; G02B 26/0841; G02B 26/105; G02B 26/085; G02B 26/0858; G02B 26/0833; G02B 26/101; A61B 3/14; B81B 3/0083; B81B 3/0086; B81B 2201/04
USPC .... 359/846, 849, 198.1–199.4, 200.6–200.8, 359/202.1, 221.2, 223.1–225.1, 226.2, 359/904, 290–295, 838, 871, 872; 351/206; 250/204, 559.06, 559.29, 230, 250/234; 347/255–260; 353/39, 98–99; 385/15–18, 22; 398/12, 19, 45
See application file for complete search history.

(56) References Cited

U.S. PATENT DOCUMENTS

| | | | |
|---|---|---|---|
| 4,239,343 A * | 12/1980 | Wrench ................. | G02B 26/06 359/849 |
| 6,384,952 B1 | 5/2002 | Clark | |
| 6,952,304 B2 | 10/2005 | Mushika | |
| 7,929,195 B2 | 4/2011 | Bifano | |
| 8,087,779 B2 * | 1/2012 | Levecq ........................ | 351/205 |

(Continued)

FOREIGN PATENT DOCUMENTS

| | | |
|---|---|---|
| EP | 2453570 A2 | 5/2012 |
| FR | 2958415 A1 | 10/2011 |

(Continued)

OTHER PUBLICATIONS

Extended European Search Report dated 16.04.2014 Reference EP71428 App. 14154610.1-1562.

*Primary Examiner* — Scott J Sugarman
*Assistant Examiner* — Kristina Deherrera
(74) *Attorney, Agent, or Firm* — Canon U.S.A., Inc., IP Division

(57) ABSTRACT

A deformable mirror includes a mirror substrate having a continuous reflective surface and a plurality of actuators connected to the mirror substrate at a plurality of coupling portions. In the deformable mirror, the mirror substrate has first regions and a second region thicker than the first regions and the first regions are formed around the coupling portions.

32 Claims, 13 Drawing Sheets

(56) References Cited

U.S. PATENT DOCUMENTS

| | | |
|---|---|---|
| 2005/0046504 A1 | 3/2005 | Xiaoyu |
| 2005/0207037 A1 | 9/2005 | Minegishi |
| 2006/0050419 A1 | 3/2006 | Ealey |
| 2006/0058682 A1 | 3/2006 | Miller |
| 2007/0002472 A1 | 1/2007 | Nagashima |
| 2007/0137989 A1 | 6/2007 | Divoux |
| 2007/0297042 A1 | 12/2007 | Bifano |
| 2010/0027142 A1 | 2/2010 | Beresnev |
| 2010/0033704 A1 | 2/2010 | Shiraishi |
| 2011/0211268 A1 | 9/2011 | Camet |

FOREIGN PATENT DOCUMENTS

| | | | |
|---|---|---|---|
| JP | 2003084218 | * | 3/2003 |
| JP | 2003084218 A | | 3/2003 |
| JP | 2008040304 A | | 2/2008 |

* cited by examiner

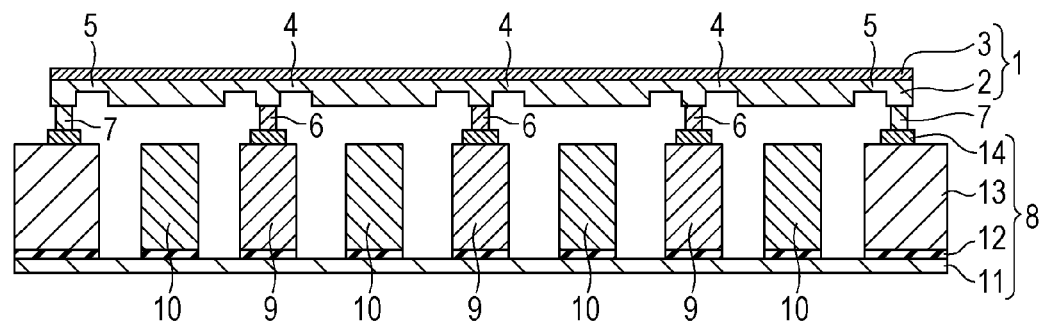
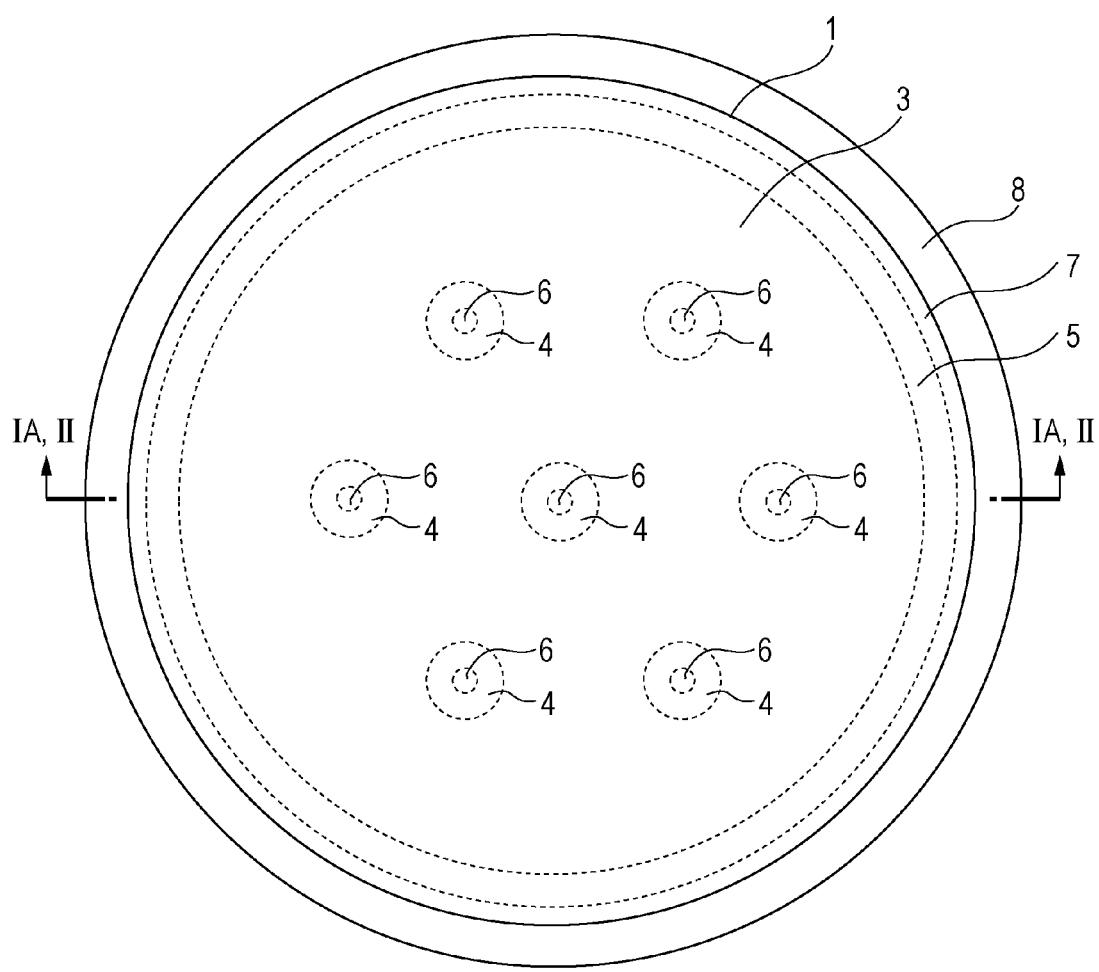

FIG. 4B  S101 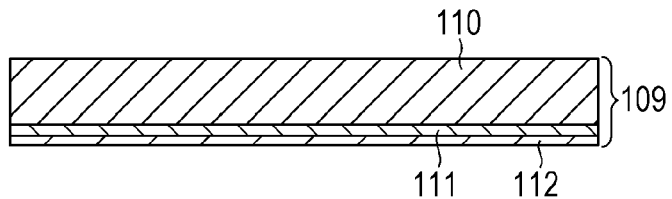
FIG. 4C  S102 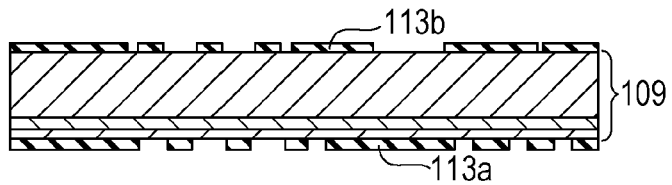
FIG. 4D  S103 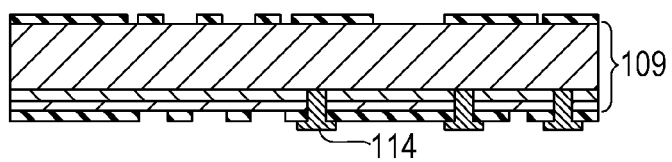
FIG. 4E  S104 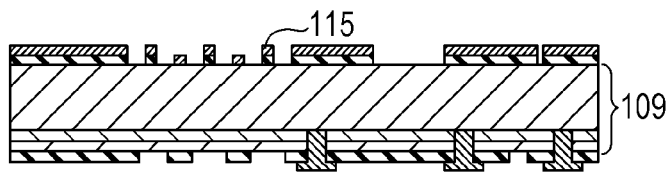
FIG. 4F  S105 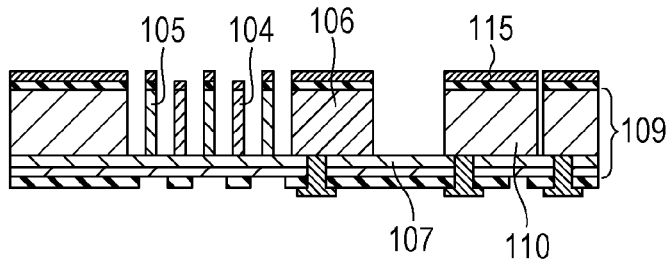
FIG. 4G  S106 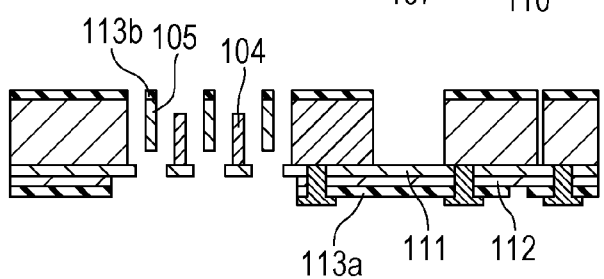
FIG. 4H  S107 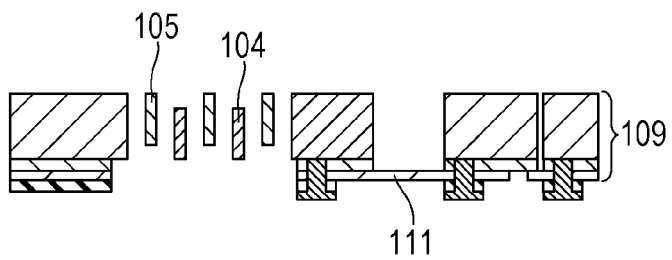

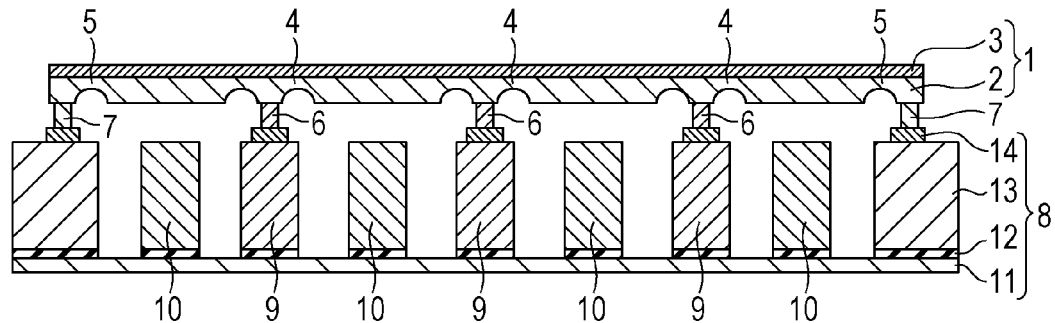
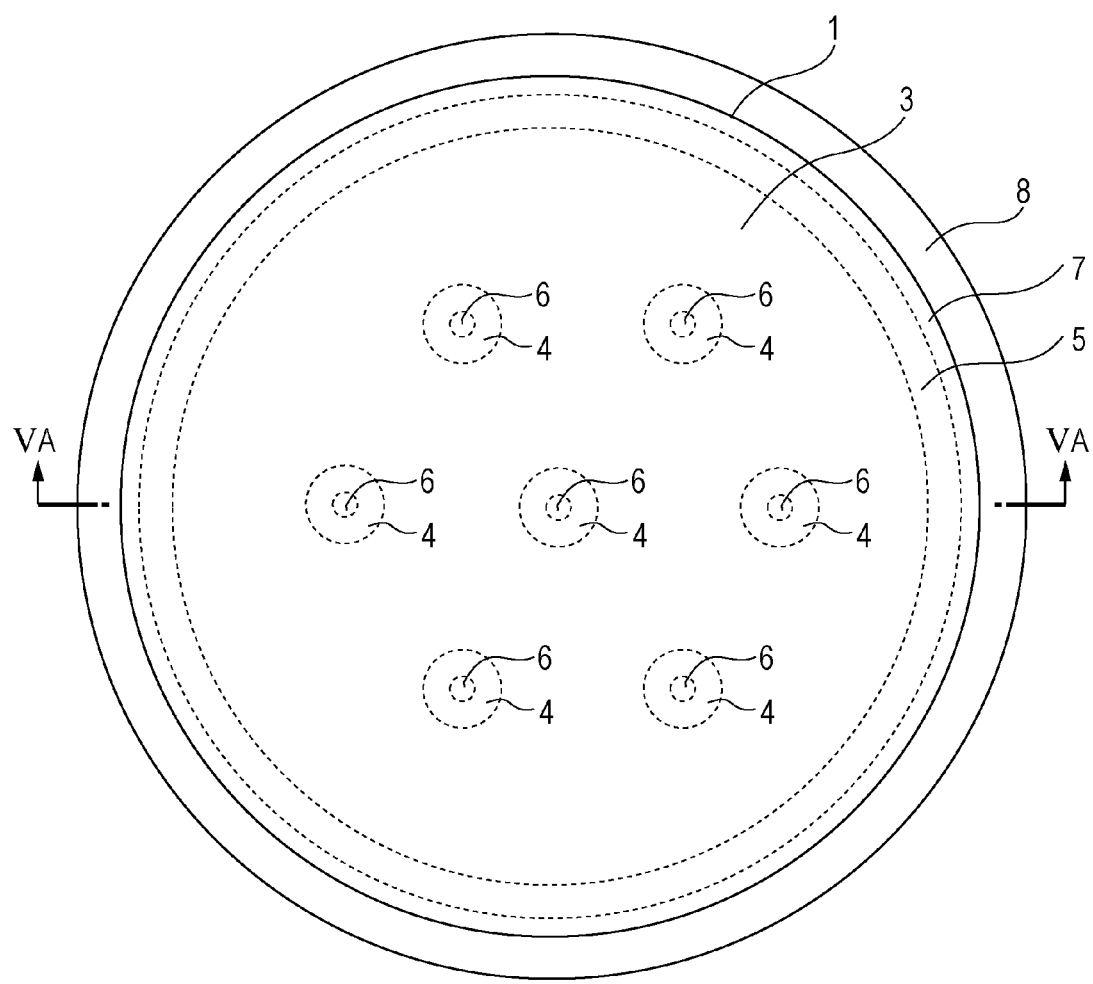

DEFORMABLE MIRROR AND METHOD FOR MANUFACTURING THE SAME

BACKGROUND OF THE INVENTION

Field of the Invention

The present invention relates to a deformable mirror and a method for manufacturing the same.

Description of the Related Art

A deformable mirror is an optical device and usable as a wavefront aberration correction device in adaptive optics. The deformable mirror is thus expected to be applicable to various uses in the optical field including a funduscope and an astronomical telescope. U.S. Pat. No. 7,929,195 discloses a deformable mirror in which a deformable layer having a certain film thickness and including a reflective layer is connected to a plurality of electrostatic actuators via a plurality of coupling portions. The deformable mirror is formed into an appropriate shape by driving the electrostatic actuators so that multiple portions of the deformable layer connected to the actuators are individually pulled substantially downward in the vertical direction. Japanese Patent Laid-Open No. 2008-40304 discloses a deformable mirror used in an optical pickup device of an optical disc information input-output device. Specifically, a deformable mirror connected to actuators via protrusions formed on the mirror substrate is disclosed.

In the deformable mirror disclosed in U.S. Pat. No. 7,929,195, portions of the deformable layer around the coupling portions are deformed at a smaller angle than an ideal shape due to the flat shape of the coupling portions, whereby the surface shape of the deformable mirror deviates from an ideal surface shape.

For example, FIG. 6 illustrates simulation results of deformed mirror shapes of models having a mirror shape similar to those according to U.S. Pat. No. 7,929,195, when a plurality of actuators are driven so as to form an ideal surface shape indicated by the line x, where the simulated shapes are represented by the lines b and c. The line b represents the result obtained when the mirror thickness is 1.2 μm and the line c represents the result obtained when the mirror thickness is 3.0 μm. FIG. 6 shows that the mirror shape according to U.S. Pat. No. 7,929,195 deviates from an ideal surface shape to a large degree regardless of the thickness of the mirror substrate. Thus, a wavefront aberration optical system including such a deformable mirror is unable to completely correct aberration due to the deviation of the surface shape from the ideal surface shape and requires improvement in optical characteristics such as resolving power.

Also in the deformable mirror disclosed in Japanese Patent Laid-Open No. 2008-40304, a deformable portion of the mirror substrate has a uniform thickness except for the protrusions connected to the actuators. Consequently, similarly to the deformable mirror disclosed in U.S. Pat. No. 7,929,195, the shape of the mirror substrate deviates from an ideal surface shape due to a decrease in amount of deformation around the portions connected to the actuators.

SUMMARY OF THE INVENTION

The present invention provides a deformable mirror that has a shape approximate to an ideal surface shape and that can improve optical characteristics, such as resolving power, when included in a wavefront aberration optical system. The present invention also provides a method for manufacturing the deformable mirror.

A deformable mirror according to an embodiment of the invention includes a mirror substrate having a continuous reflective surface and a plurality of actuators connected to the mirror substrate via a plurality of coupling portions. The mirror substrate has first regions and a second region thicker than the first regions and the first regions are formed around the coupling portions.

A method for manufacturing a deformable mirror including a mirror substrate having a continuous reflective surface and a plurality of actuators connected to the mirror substrate via a plurality of coupling portions, the method including: a step of preparing a first substrate including a silicon layer, an insulator layer, and a handling layer arranged in this order; a step of forming thin regions in the silicon layer around regions of the silicon layer that are to serve as the coupling portions, the thin regions having a smaller thickness than other portions of the silicon layer; a step of forming the plurality of actuators on a second substrate; a step of connecting the first substrate and the second substrate together by coupling coupling portions of the silicon layer with coupling portions of the actuators; and a step of removing the handling layer and the insulator layer of the first substrate.

Further features of the present invention will become apparent from the following description of exemplary embodiments with reference to the attached drawings.

BRIEF DESCRIPTION OF THE DRAWINGS

FIGS. 1A and 1B illustrate a deformable mirror according to a first embodiment of the invention in a cross section and a plan view, respectively.

FIG. 4A illustrates an actuator unit of the deformable mirror according to the embodiment of the invention in a bottom view and FIGS. 4B to 4h illustrate steps of a method for manufacturing the actuator unit in cross sections.

FIGS. 5A and 5B illustrate a deformable mirror according to another modified example of the invention in a cross section and a plan view, respectively.

Figure 2A:
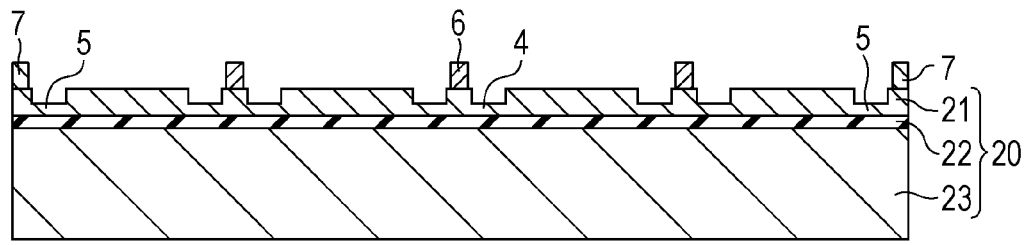
FIGS. 2A to 2D illustrate steps of a method for manufacturing a deformable mirror according to a second embodiment of the invention in cross sections.

12B is a graph showing cross-sectional profiles of the mirror surfaces resulting from the simulation.

DESCRIPTION OF THE EMBODIMENTS

In a deformable mirror according to an embodiment of the invention, actuators are connected with a mirror substrate having a reflective surface at coupling portions of the mirror substrate. Thin portions (first regions) thinner than other portions (second regions) are formed at portions of the mirror substrate surrounding the coupling portions and on the opposite side to the reflective surface in order to facilitate deformation of the mirror substrate around the coupling portions. Here, the coupling portions refer to portions of the mirror substrate to which the actuators are coupled. In the following embodiments or examples, portions at which posts and/or pads are formed serve as coupling portions.

In the following embodiments or examples, electrostatic comb-drive actuators are used but other publicly-known structures may be used in accordance with the purpose of use of the deformable mirror. Such actuators as those used in U.S. Pat. No. 7,929,195 and Japanese Patent Laid-Open No. 2008-40304 may be also used.

Now, the structure, operations, and effects of the invention are described using a deformable mirror and a method for manufacturing the deformable mirror according to embodiments of the invention.

Structure of Deformable Mirror

Referring to FIGS. 1A and 1B, a deformable mirror according to an embodiment of the invention will be described. FIG. 1B is a plan view of the deformable mirror and FIG. 1A is a cross sectional view of the deformable mirror taken along the line IA, II-IA, II of FIG. 1B. The deformable mirror includes a mirror unit 1, including a mirror substrate 2 and a reflective film 3, and an actuator unit 8. The mirror unit 1 is connected to the actuator unit 8 via posts 6 and a circumferential coupling member 7. Each post 6 is coupled to a corresponding one of the coupling portions of the mirror substrate 2 and a coupling pad 14 disposed on a corresponding one of movable portions 9, serving as coupling portions of the actuator unit 8. The circumferential coupling member 7 is coupled to the circumferential coupling portion at the circumference of the mirror substrate 2 and a corresponding one of the coupling pads 14 disposed on a circumferential immovable portion 13 of the actuator unit 8. The circumference of the mirror substrate 2 and the circumferential immovable portions 13 of the actuator unit 8 may or may not be coupled together as needed.

In the deformable mirror illustrated in FIG. 1B, seven actuators are connected to the single mirror unit 1 having a continuous reflective surface. As illustrated in FIGS. 1A and 1B, first regions (thin portions) 4 and 5 in which the mirror substrate 2 is thinner are formed around the coupling portions of the mirror substrate 2 on the opposite side to the reflective surface and on the inner periphery of the circumferential coupling portion. A second region, in which the thickness of the mirror substrate 2 is larger than the thickness of the mirror substrate 2 in the first regions, is formed around the first regions. In other words, the mirror unit 1 has first regions, in which the mirror substrate 2 has a certain thickness, around the coupling portions and a second region, in which the thickness of the mirror substrate is larger than that in the first regions, between the coupling portions. The thickness of the mirror substrate 2 at the coupling portions may be the same as that in the first region (thin portions) 4 or that in the second region. However, from the manufacturing point of view described below, the thickness of the mirror substrate 2 at the coupling portions may be larger than that in the first region (thin portions) 4 and the same as that in the second region. In the following description, the configuration in which the thickness of the mirror substrate 2 at the coupling portions are the same as that in the second region is mainly described.

The thin portion 5 is provided for facilitating deformation of the mirror substrate 2 at the circumferential coupling portion. If the mirror substrate 2 is not coupled to the actuator unit 8 at the circumference, the thin portion 5 may not be formed at the circumference.

The actuator unit 8 includes immovable portions 10, the circumferential immovable portion 13, and the movable portions 9, which are connected together via an elastic body 11. An insulating layer 12 is interposed between the elastic body 11 and each of the immovable portions 10, the circumferential immovable portion 13, and the movable portions 9 so as to electrically insulate each other. In accordance with a desired shape of the mirror unit 1, a voltage is applied to the movable portions 9 via wiring, not illustrated, individually connected to the movable portions 9. Consequently, the movable portions 9 are individually displaced in the vertical direction with respect to the reflective surface to which the voltage is not applied, so that the mirror unit 1 is deformed. The immovable portions 10, the movable portions 9, other members of the actuator unit 8 will be described in detail below referring to FIGS. 4A to 4H.

For example, by displacing the movable portion 9 at the center of the mirror unit 1 downward, the mirror unit 1 can be formed into a recessed shape. Here, since the mirror unit 1 has the thin first regions (thin portions) 4 and 5 in the mirror substrate 2 around the posts 6 and on the inner periphery of the circumferential coupling member 7, the mirror substrate 2 is easily and flexibly deformed around the posts 6 and on the inner periphery of the circumferential coupling member 7. Moreover, since the mirror substrate 2 in the second region extending between the posts 6 has a larger thickness and a higher rigidity than in the first region, the mirror substrate 2 between the posts 6 can be deformed into a smooth curve. Consequently, the shape of the mirror unit 1 can be approximated to a desired ideal surface shape.

Figure 6:
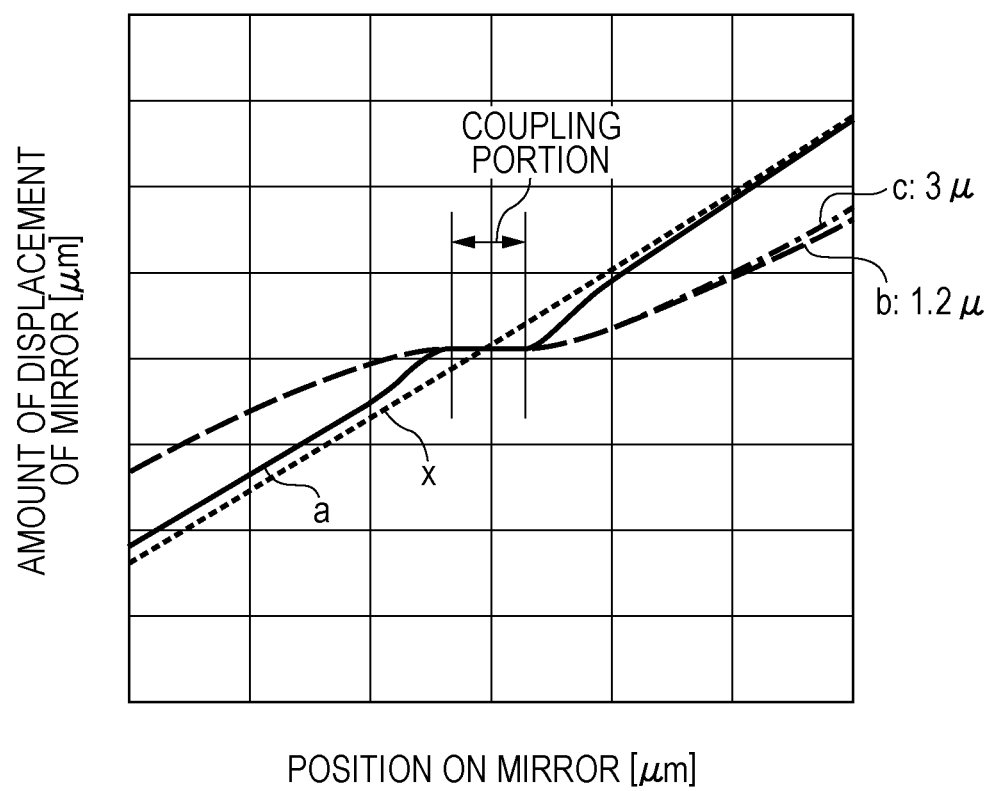
FIG. 6 is a graph showing cross-sectional profiles of mirror surfaces resulting from the finite-element simulation.

In FIG. 6, the line a indicates a mirror shape according to the configuration of the invention resulting from a simulation in which the plurality of actuators are driven so as to form an ideal surface shape drawn with the line x in FIG. 6.

Silicon is assumed as a material of the mirror substrate. The thickness of the mirror substrate is taken as 1.2 µm in the first regions around the coupling portions and 5 µm in the second region. As seen in the graph, the deformable mirror according to the embodiment of the invention can have a shape deviated from the ideal surface shape to a lesser degree than the deformable mirror disclosed in U.S. Pat. No. 7,929,195.

Although FIG. 1B illustrates a configuration in which seven actuators are connected to the mirror unit 1 having a continuous reflective surface, this configuration is merely an example. By increasing the number of actuators, more complex mirror surface shape can be formed highly accurately.

Figure 3A:
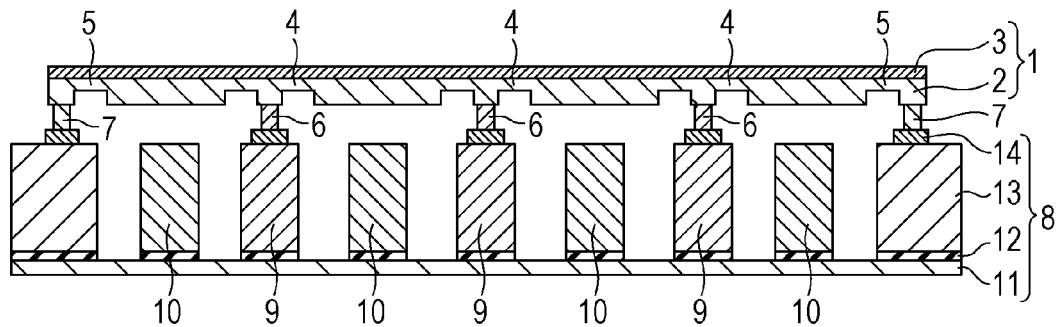
FIGS. 3A and 3B illustrate a deformable mirror according to a modified example of the invention in a cross section and a plan view, respectively.
Figure 3B:
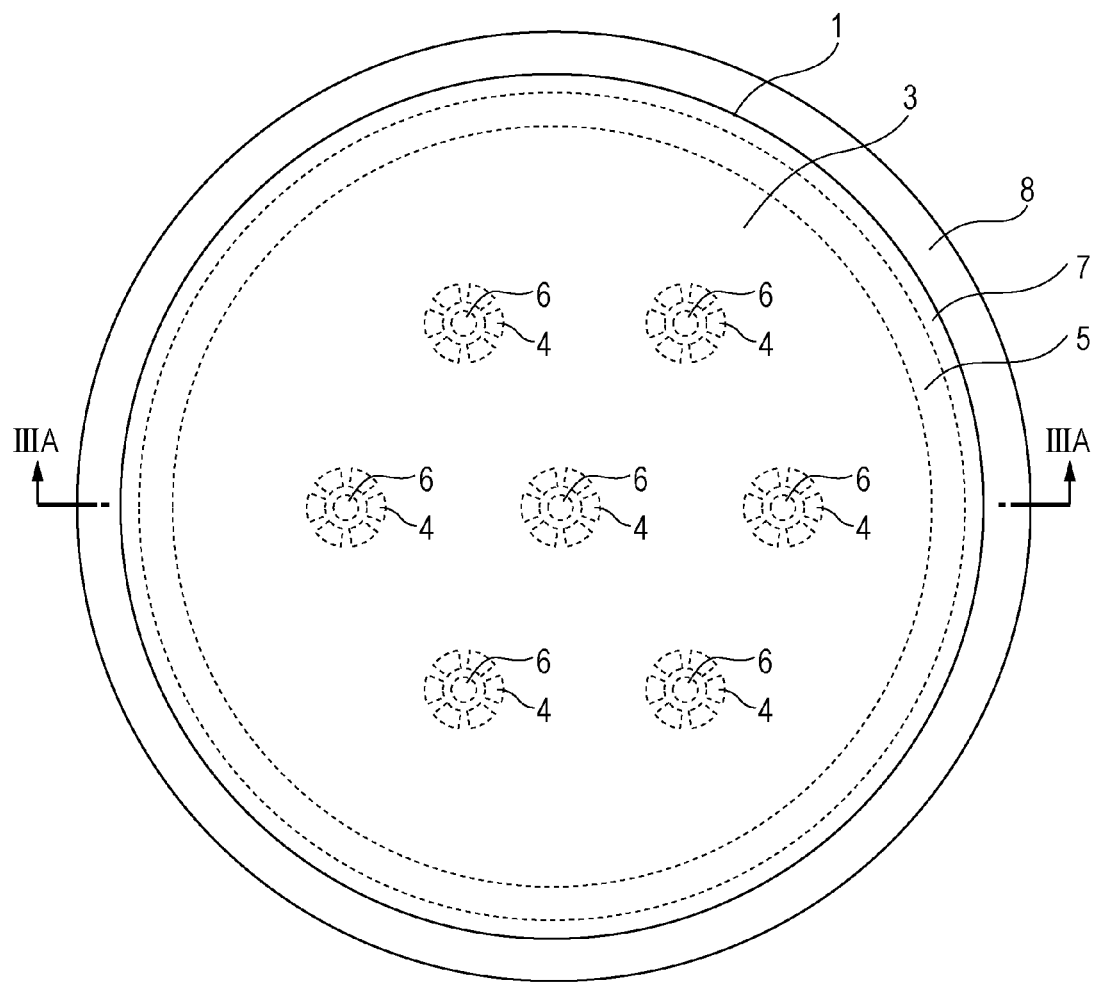

In FIGS. 1A and 1B, each thin portion is formed into a continuous groove surrounding the corresponding coupling portion, that is, into a ring-shaped groove, but is not limited to this shape. For example, as illustrated in FIG. 3B, thin portions may be symmetrically and discretely disposed around each coupling portion. In this case, thin portions may be formed on the line connecting adjacent coupling portions. In terms of reinforcement of the physical strength of the mirror substrate, the thin portions may be discretely provided. However, in order to approximate the mirror shape to the ideal shape, the grooves may be ring-shaped as illustrated in FIG. 1B.

In FIG. 1A, portions of the mirror substrate 2 thicker than the thin portions 4 and 5, that is, the second region and the coupling portions have a rectangular cross section. However, as illustrated in FIG. 5A, the thickness of the mirror substrate 2 may be continuously changed at or around the border between each thin portion (first region) and a thick portion (second region), particularly, at the corners of the recess above the thin portion. In other words, the thin portion in FIG. 5A has a curved cross section to avoid stress concentration at or around the border between the thin portion and a portion of the mirror substrate surrounding the thin portion. The deformable mirror can thus have higher durability because the force exerted on the border between the thin portion 4 and the thick portion is dispersed and less likely to be concentrated when the mirror unit 1 is deformed by driving the actuator unit 8. In this manner, the deformable mirror according to the embodiment can have a higher durability as well as a shape more approximate to the ideal surface shape of the mirror.

Figure 12A:
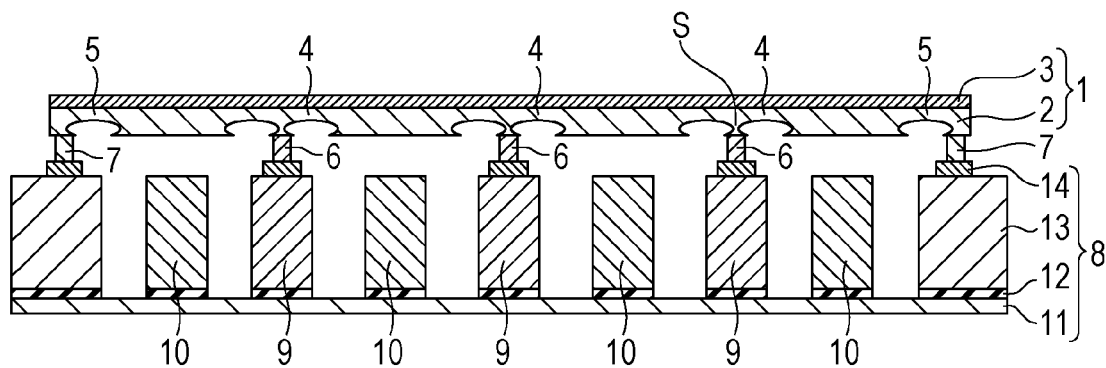
FIG. 12A is a cross-sectional view of a deformable mirror according to a modified example of the invention and FIG.

Alternatively, as illustrated in FIG. 12A, the mirror substrate 2 at the coupling portions, which are portions S, may have a large thickness and the diameter of the portions S may decrease from the side adjacent to the posts 6 toward the side adjacent to the reflective surface 3. The mirror substrate 2 may be formed into the above-described shape by thinning portions of the mirror substrate 2 around regions that are to become coupling portions than other portions and then by etching the mirror substrate 2 at the coupling portions in the direction parallel to the reflective surface 3 of the mirror substrate 2.

Figure 12B:
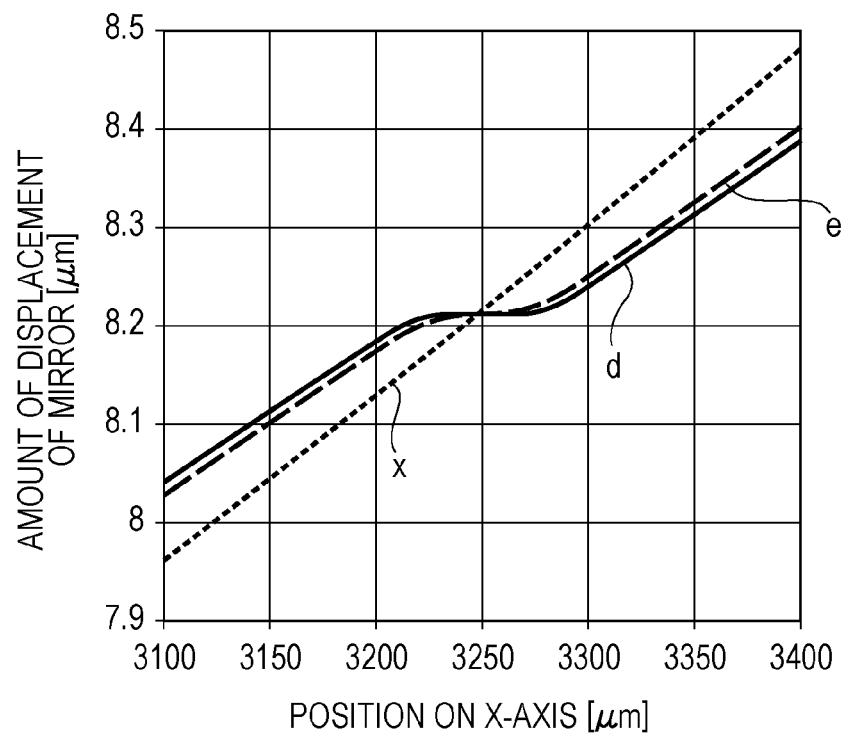

FIG. 12B illustrates a cross-sectional profile of a modified portion S, which is a thick portion of the mirror substrate 2 at the coupling portion, at the deformation of the mirror resulting from the simulation. The line x represents an ideal shape. The line d represents the profile of the mirror surface obtained when the portion S, which is a thick portion of the mirror substrate 2 at the coupling portion, has a uniform diameter as in the case of the mirror substrate 2 illustrated in FIG. 1A. The line e represents the profile of the mirror surface obtained when the portion S has the shape as illustrated in FIG. 12A. In either of the cases corresponding to the lines d and e, the conditions of the deformable mirror such as the thickness of the silicon layer or the amount of movement of the actuators are the same.

The simulation results show that the line e is closer to the ideal shape of the mirror surface than the line d. The shape illustrated in FIG. 12A may be effectively used to address the situation where the mirror substrate 2 has a relatively small thickness or where the dimensions of the posts 6 coupled to the coupling portions are large.

Method for Manufacturing Deformable Mirror

Referring now to FIGS. 2A to 2D, a method for manufacturing a deformable mirror according to a second embodiment of the invention will be described now.

FIGS. 2A to 2D illustrate steps of the method for manufacturing a deformable mirror according to a second embodiment in cross sections taken along the line IA, II-IA, II of FIG. 1B. The method for manufacturing a deformable mirror according to the embodiment involves forming thin portions in a silicon-on-insulator (SOI) layer 21 of a silicon-on-insulator (SOI) substrate 20, serving as a mirror substrate, and placing the mirror substrate on the actuator unit.

Firstly, as an example of a first substrate including a silicon layer, an insulator layer, and a handling layer, an SOI substrate 20 is prepared. The SOI substrate 20 includes an SOI layer 21 made of silicon, a handling layer 23, and a buried oxide (BOX) layer 22 made of silicon oxide and interposed between the SOI layer 21 and the handling layer 23. Subsequently, as illustrated in FIG. 2A, thin portions 4 and 5, serving as first regions, are formed in the SOI layer 21, serving as the mirror substrate, posts 6 are formed at the coupling portions of the SOI layer 21, and a circumferential coupling member 7 is formed at the circumferential coupling portion of the SOI layer 21. To form the thin portions 4 and 5 serving as first regions, an etching mask, not illustrated, having openings at corresponding positions at which the thin portions 4 and 5 are to be formed is formed on the SOI layer 21. The etching mask may be a resist pattern formed by photolithography.

Subsequently, grooves are formed by dry etching using the resist mask as an etching mask. The resist mask is then removed by, for example, oxygen asking, so that the thin portions 4 and 5 are formed in the SOI layer 21. The silicon depth control during etching the SOI layer 21 is time-based. Here, the silicon etching rate may be slow so as to allow control of the etching end point without haste. In this manner, the thin portions surrounding the coupling portions are formed in the mirror substrate 2 before the mirror unit 1 is connected to the actuator unit 8 and before the handling layer is removed. Thus, the thin portions can be relatively easily formed.

Thereafter, the posts 6 are formed on the SOI layer 21, serving as the mirror substrate, at the coupling portions surrounded by the thin portions 4 and the circumferential coupling member 7 is formed at the circumferential coupling portion on the outer periphery of the thin portions 5. Consequently, the structure including thin portions around the posts 6 and the circumferential coupling member 7 is formed as illustrated in FIG. 2A. The posts 6 and the circumferential coupling member 7 are formed by, for example, forming Au bumps by electroplating. Although Au bumps are taken as examples of the posts 6 and the circumferential coupling member 7, the posts 6 and the circumferential coupling member 7 may be formed by other methods. Depending on the subsequent coupling method, solder or other materials may be used, instead.

The thickness of the mirror substrate at the thin portions, the size and the shape of each thin portion, the size and the pitch of the coupling portions, and other conditions may be appropriately determined depending on the purpose of use on the basis of parameters such as an allowable amount of deviation of the surface shape from an ideal surface shape that is allowed by the wavefront aberration correction device.

An increase in thickness of the thin portions and the thick portion improves the strength of the mirror but requires the actuators to exert a larger force for deforming the mirror. Thus, the thin portions and the thick portion may have a minimum possible thicknesses within such a range that the mirror is prevented from being broken, considering other conditions including the maximum amount of deformation required for the wavefront aberration correction device, the pitch of the coupling portions, an allowable amount of deviation of the surface shape from an ideal surface shape, the driving force of the actuators, and the Young's modulus of the mirror. Similarly to the coupling portions, since the thin portions (first regions) are portions where deviation from the ideal surface shape occurs and that have a smaller strength than the thick portion, the thin portions may have a minimum width.

The mirror substrate at the coupling portions may have the same thickness as the thin portions. In this case, if a bump is placed at an incorrect position on a thin portion, the width of the thin portion surrounding the bump may become asymmetrical. To avoid this situation, the thickness at the coupling portions may remain the same as the thickness of the SOI layer and the thin portions may be formed only around the coupling portions in the manner as described above, so that the width of each thin portion can remain unchanged after the thin portion has been formed.

Figure 2B:
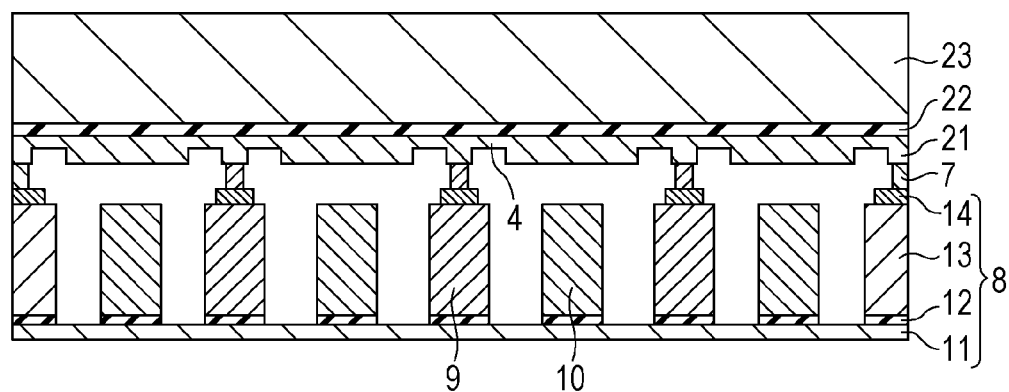

Subsequently, as illustrated in FIG. 2B, the actuator unit 8 that deforms the mirror shape is formed on a second substrate. The actuator unit 8 is, for example, an electrostatic comb-drive actuator and includes movable portions 9, immovable portions 10, and a circumferential immovable portion 13. The actuator unit 8 also includes pads 14 on the movable portions 9 and the circumferential immovable portion 13 at coupling portions that are coupled with the posts 6 and the circumferential coupling member 7 disposed at the coupling portions of the mirror unit 1. FIG. 2B does not include the illustration of an electrostatic comb-drive portion. Although the movable portions 9, the immovable portions 10, and the circumferential immovable portion 13 are connected together via the elastic body 11, they are insulated one another via the insulating layer 12. The movable portions 9 can be individually driven in response to individual application of voltages to the movable portions 9 via wiring, not illustrated.

Subsequently, the first substrate having the mirror substrate in which the thin portions 4 and 5 are formed and the second substrate including the actuator unit 8 are connected together via multiple posts 6, the circumferential coupling member 7, and the pads 14 on the actuator unit 8. In the case where the posts 6 and the circumferential coupling member 7 on the SOI layer are made of Au bumps and the pads 14 on the actuator unit 8 are Au pads, the Au bumps and the Au pads may be coupled together by room-temperature Au—Au surface activation coupling, specifically, by removing organic matter on the surfaces of the Au bumps and the Au pads, for example, using Ar plasma for activating the surfaces and then coupling the Au bumps and the Au pads together. Although the room-temperature surface activation coupling is used as a coupling method in the embodiment, the present invention is not limited to this method. Examples of other conceivable methods include solder-bump coupling in which solder bumps are formed as the posts and aluminum (Al) is selected as a material of the pads.

Figure 2C:
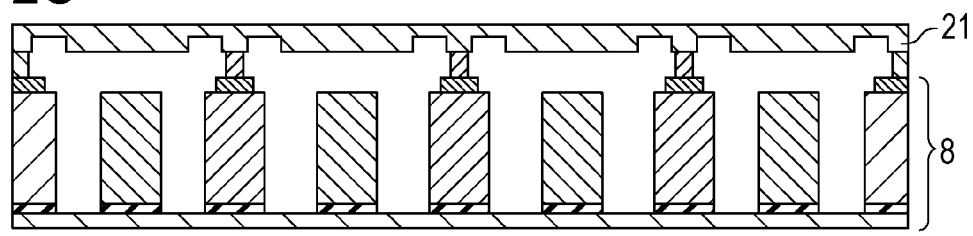

Then, as illustrated in FIG. 2C, the handling layer 23 and the insulator layer (BOX layer) 22 of the SOI substrate 20 serving as the first substrate are removed. Thus, a structure in which the mirror substrate 21, which is the SOI layer, is connected to the actuator unit 8 is completed. The handling layer 23 is removed by, for example, silicon dry etching. The etching end point is controlled using plasma emission spectrometry and the BOX layer 22 of the SOI substrate 20 is used as an etching stopper layer. Since a high etching selection ratio between the handling layer and the BOX layer 22 serving as an etching stopper layer is used in this silicon dry etching, the BOX layer 22 protects the SOI layer 21, thereby preventing the SOI layer 21 from being etched. The handling layer 23 may be removed by wet etching using tetramethyl ammonium hydroxide (TMAH).

Figure 2D:
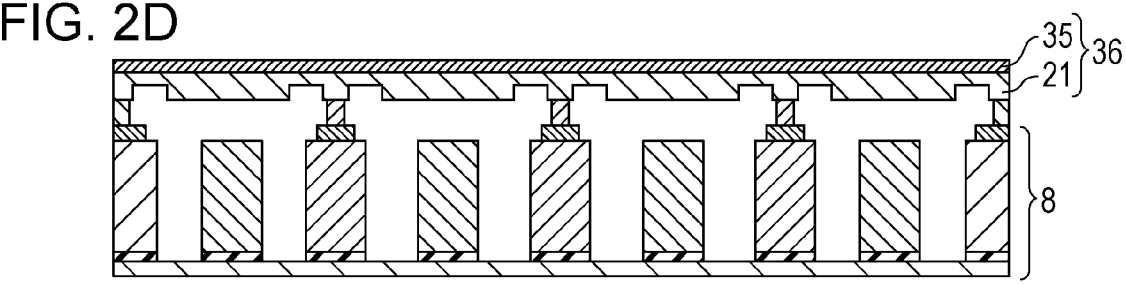

The BOX layer 22 is removed by wet etching using, for example, buffered hydrogen fluoride (BHF). Here, the etching selection ratio between the SOI layer (mirror substrate) 21, which underlies the BOX layer 22, and the BOX layer 22 is high, and the SOI layer is thus negligibly etched. The BOX layer 22 can be consequently removed without damaging the mirror substrate 21. Alternatively, the BOX layer 22 may be removed by dry etching using vapor hydrogen fluoride. Subsequently, as illustrated in FIG. 2D, a reflective film 35 is formed on the mirror substrate 21 to be used as a mirror member 36 having a higher reflectivity than the mirror unit 1.

As described above, the method for manufacturing a deformable mirror according to the embodiment includes at least the following steps: preparing a first substrate including a SOI layer, an insulator layer, and a handling layer; forming thin portions (first regions) around portions of the SOI layer that are to be used as the coupling portions, the first regions being thinner than the other region (second region); forming a plurality of actuators on a second substrate; connecting the first substrate and the second substrate together by coupling the coupling portions of the SOI layer surrounded by the thin portions with coupling portions of the actuators; and removing the handling layer and the insulator layer of the first substrate. This method facilitates formation of a deformable mirror having thin portions around coupling portions that form the coupling portions of the mirror substrate. In this embodiment, the coupling portions of the SOI layer and the actuators are coupled together via posts and pads.

Method for Manufacturing Actuator Unit

Referring now to FIGS. 4A to 4H, a configuration of an actuator unit for which an electrostatic comb-drive actuator suitable for the deformable mirror according to an embodiment of the invention is used and a method for manufacturing the actuator unit will be described.

Using an electrostatic comb-drive actuator as the actuator unit 8 is advantageous in terms of fine control of the amount of displacement since the displacement stroke (maximum amount of displacement) is relatively small, for example, 10 μm.

Figure 4A:
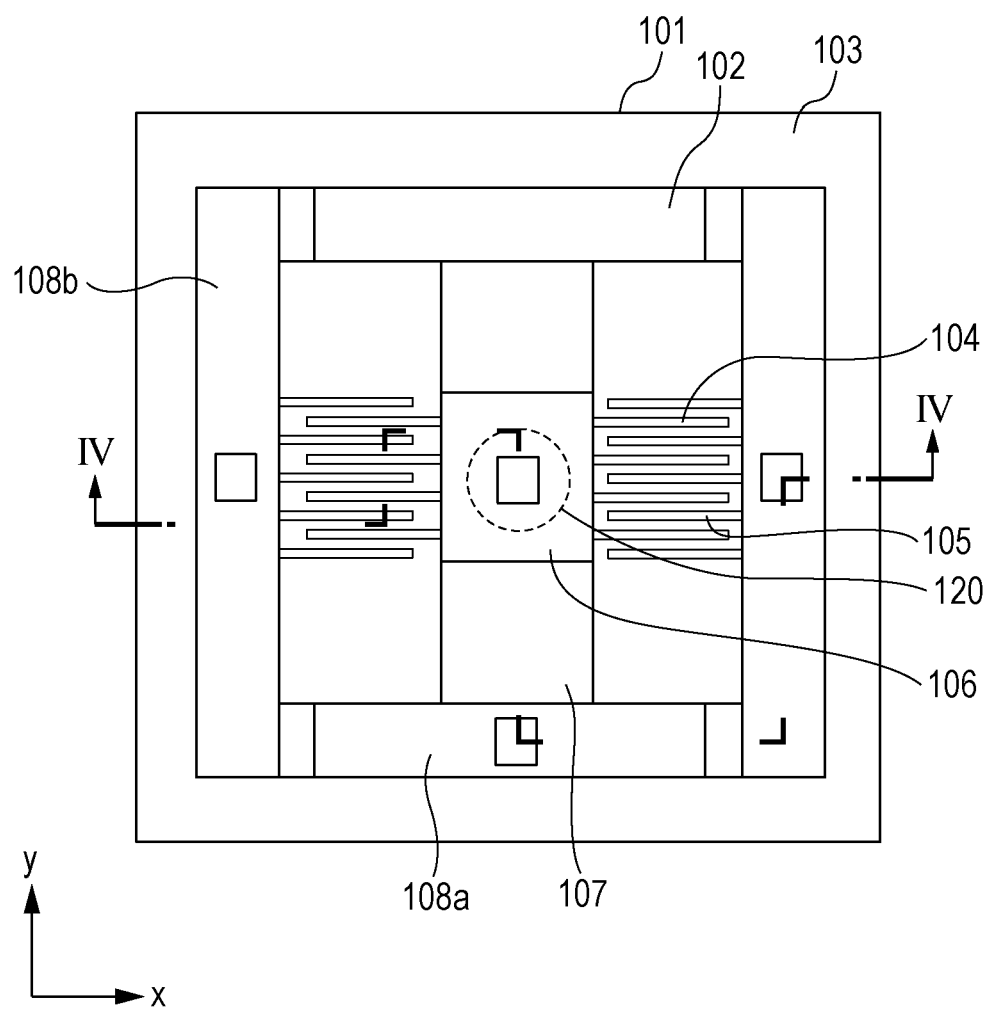

FIG. 4A is a plan view of a deformable mirror 101 viewed from the actuator unit 102. Although the deformable mirror 101 includes a plurality of actuators, as illustrated in FIGS. 1A and 1B, FIG. 4A illustrates only one of the actuators. FIGS. 4B to 4H are cross-sectional views of the deformable mirror 101 taken along the line IV-IV in FIG. 4A and illustrate steps of a method for manufacturing the configuration illustrated in FIG. 4A. The deformable mirror 101 to be manufactured includes an actuator unit 102 and a mirror unit 103. The mirror unit 103 has an optical reflective function with which the unit reflects light that is to be corrected. The mirror unit 103 includes a reflective surface for reflecting light. The mirror unit 103 is disposed so as to cover the actuator unit 102.

The actuator unit 102 includes movable comb-drive electrodes 104, immovable comb-drive electrodes 105, a movable portion 106, an elastic body 107, and immovable portions 108 (108a and 108b). The movable portion 106 is coupled to the elastic body 107 and connected to the movable comb-drive electrode 104 and the mirror unit 103. The coupling portions of the movable portion 106 are connected to the coupling portions of the mirror unit 103. One end of the elastic body 107 is fixed to the immovable portion 108a. The movable comb-drive electrodes 104 and the elastic body 107 are each connected to a side wall of the movable portion 106. The mirror unit 103 is connected to an upper surface of the movable portion 106 via the coupling portions. The movable comb-drive electrodes 104 protrude in the x direction from the side walls of the movable portion 106 parallel to the y-z plane (plane perpendicular to the x axis) while the immovable comb-drive electrodes 105 protrude in the x direction from the side walls of the immovable portions 108b parallel to the y-z plane. Specifically, the side walls of the movable portion 106 to which the movable comb-drive electrodes 104 are attached and the side walls of the immovable portion 108 to which the immovable comb-drive electrodes 105 are attached are disposed so that the movable comb-drive electrodes 104 and the immovable comb-drive electrodes 105 face one another. The comb teeth of the electrodes 104 and 105 are alternately arranged with gaps therebetween.

Now, a method for manufacturing the actuator unit 102 will be described. Here, an example where a plurality of actuators are simultaneously formed by processing a SOI substrate is described. The drawings, however, illustrate only one actuator.

Firstly, as illustrated in FIG. 4B, a SOI substrate 109 is prepared (Step S101). Then, as illustrated in FIG. 4C, patterns of insulating layers 113 are formed on both sides of the SOI substrate 109 (Step S102). Specifically, silicon oxide ($SiO_2$) is formed by thermal oxidization as insulating layers 113 and then resist patterns (not illustrated) are formed thereon. The insulating layers 113 are etched using the resist patterns as masks. Here, the insulating layers 113 are etched by plasma etching using, for example, a fluorocarbon gases, such as tetrafluoromethane ($CF_4$), difluoromethane ($CH_2F_2$), and trifluoromethane ($CHF_3$). These fluorocarbon gases may be used individually or after being mixed with other fluorocarbon gases or inert gases such as argon (Ar) and helium (He).

Thereafter, as illustrated in FIG. 4D, a penetrating electrode 114 having a contact-hole pattern is formed (Step S103). Firstly, a resist pattern, not illustrated, is formed on the back surface of the SOI substrate 109. Using the resist pattern as a mask, a silicon active layer 112 and a BOX layer 111 are etched to form through-holes. After layers of titanium (Ti) and gold (Au), serving as the materials of the electrodes, are formed in a lamination manner, a resist pattern (not illustrated) is formed thereon. Using the resist pattern as a mask, the layers of gold (Au) and titanium (Ti) are etched.

Subsequently, as illustrated in FIG. 4E, a mask for forming comb teeth is formed (Step S104). A resist pattern 115 is formed on the surface of the handling layer 110 of the SOI substrate 109 and the insulating layer 113b on the handling layer 110 is etched into a pattern. The insulating layer 113b is etched by plasma etching using fluorocarbon gases described in Step S102. Subsequently, as illustrated in FIG. 4F, movable comb-drive electrodes 104 and immovable comb-drive electrodes 105 are formed from the handling layer 110 (Step S105). The handling layer 110 is etched using the resist pattern 115 and the insulating layer 113b formed in Step S104 as masks. To form a desired comb-teeth shape by etching the handling layer 110, inductively-coupled-plasma reactive-ion etching (ICP-RIE) or other types of etching that enable vertical etching on the surface of the handling layer is performed. With the ICP-RIE, a fine comb-teeth structure can be formed at a high aspect ratio.

Then, as illustrated in FIG. 4G, the comb teeth are formed (Step S106). In order to form the comb teeth of the immovable comb-drive electrode 105, the silicon active layer 112 is etched using an insulating layer ($SiO_2$) 113a on the back surface. Then, the BOX layer 111 is etched using the active layer 112 etched into a pattern as a mask. Further, a silicon (Si) layer of the immovable comb-drive electrode 105 is etched using the BOX layer 111 etched into a pattern as a mask. After the resist pattern 115 on the surface is removed, a silicon (Si) layer of the movable comb-drive electrode 104 is etched using the insulating layer ($SiO_2$) 113b on the surface as a mask in order to form comb teeth of the movable comb-drive electrode 104. Examples of the method for etching the silicon (Si) layers and the insulating layers include plasma etching using fluorocarbon gases described in Step S102 and the ICP-RIE described in Step S104.

Subsequently, as illustrated in FIG. 4H, the BOX layer ($SiO_2$) 111 is etched to release the movable comb-drive electrode 104 and the immovable comb-drive electrode 105 (Step S107). The BOX layer 111 is etched by selective wet-etching using, for example, 0.5% hydracid fluoride (HF). The selective etching of the BOX layer 111 may be performed using, besides hydracid fluoride, solutions containing fluorine ions including ammonium fluoride ($NH_4F$) and mixture of hydracid fluoride and hydrogen peroxide. The actuator unit and the method for manufacturing the actuator unit are described for merely exemplary purposes and the present invention is not limited to these examples.

The actuator unit 102 thus formed is coupled to the mirror unit 103, in the manner as described referring to FIGS. 2A to 2D. Specifically, a pad 120 (corresponding to the pad 14 in FIG. 2B) disposed on the coupling portion of the movable portion 106 of the actuator unit 102 is coupled to the post (corresponding to the post 6 in FIG. 2A) disposed on the coupling portion of the mirror unit 103.

As described above, the mirror substrate 2 of the mirror unit 1 may be thin with a thickness of, for example, 5 µm, because, in the deformable mirror including electrostatic comb-drive actuators, the actuators make a relatively small stroke for displacement. The coupling portions of the mirror unit 1 that are to be connected to the actuator unit 8 are disposed into, for example, a triangular grid at a pitch of, for example, 800 µm. In the case of using a thin mirror substrate 2 and small posts 6 that are to be coupled to the coupling portions, the posts 6 may pierce the deformable mirror while the deformable mirror is in operation. To prevent this from happening, the posts 6 need to have a large size. Furthermore, small posts 6 are insufficient to couple the mirror substrate 2 and the actuator unit 8 together. Thus, the posts 6 have to be large enough to couple them. The posts 6 may be relatively small Au bumps having, for example, a diameter of 20 µmφ and a height of approximately 20 µm. Since the posts 6 have such a size, the mirror substrate 2 is less likely to be deformed in areas of the mirror unit 1 around the coupling portions and on the inner periphery of the circumferential coupling portion. To address this situation, thin portions (first regions) 4 and 5 that are thinner than other portions (second region) are formed around the coupling portions and on the inner side of the circumferential coupling portion in this embodiment.

The above-described example of the manufacturing method involves processing of a plurality of actuators and the mirror substrate using photolithography with which fine patterns can be formed. Thus, the size of the patterns forming the actuators and the mirror substrate can be reduced further than the size of the patterns formed by general machine processing, whereby deviation of the mirror surface from an ideal surface shape can be minimized.

Ophthalmological Device

An adaptive optical system including the above-described deformable mirror as a wavefront aberration correction device that corrects optical aberrations will be described taking a scanning laser ophthalmoscope or an SLO, below, as an example. The SLO is an ophthalmological device that can irradiate the fundus oculi with light to observe visual cells, retinal nerve fascicles, or hemocyte movement.

Figure 7:
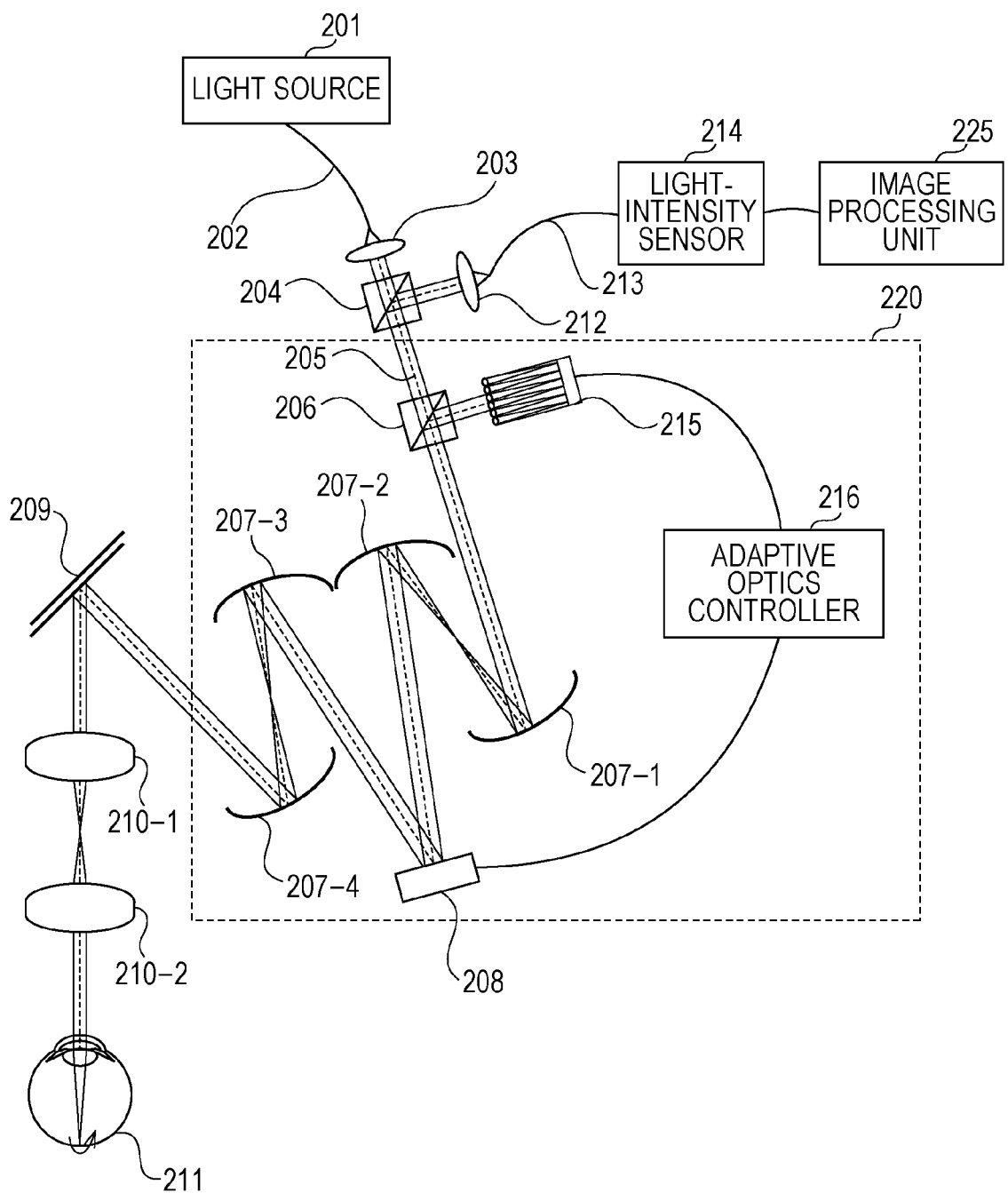
FIG. 7 schematically illustrates an adaptive optical system according to an embodiment of the invention and an ophthalmological device including the adaptive optical system.

FIG. 7 schematically illustrates a configuration of an SLO according to the embodiment.

Light emitted from a light source 201 propagates through a single mode optical fiber 202, passes through a collimator 203, and becomes a parallel light beam. The parallel light beam, which is a measurement target beam 205, passes through a beam splitter 204, serving as a beam splitting unit, and is guided to an adaptive optical system 220. Although the wavelength of light emitted from the light source 201 is not limited to be of particular wavelengths, the wavelength in the range from approximately 800 to 1500 nm is suitable for retinal imaging in order to prevent a subject from being dazzled and to maintain the resolving power.

The adaptive optical system 220 includes a beam splitter 206, which is a beam splitting unit, a wavefront sensor (aberration measuring unit) 215, a deformable mirror (wavefront aberration correction device) 208, and reflecting mirrors 207-1 to 207-4 for guiding the light beam to the splitter 206, the sensor 215, and the mirror 208. The reflecting mirrors 207-1 to 207-4 are disposed so that at least the pupil of the subject eye and the wavefront sensor 215 and the deformable mirror 208 are optically in a conjugate relationship.

The light beam that has passed through the adaptive optical system 220 is one-dimensionally or two-dimensionally scanned by an optical scanning unit 209. The measurement target beam scanned by the optical scanning unit 209 is applied to the subject eye 211 through eye lenses 210-1 and 210-2. By adjusting the positions of the eye lenses 210-1 and 210-2, a light beam appropriate for the visibility of the subject eye 211 can be applied to the subject eye 211. Here, although the lenses are used for an eyepiece unit, a spherical mirror may be used, instead.

The measurement target beam applied to the subject eye 211 is reflected or scattered by the fundus oculi or retina. The light beam reflected or scattered by the fundus oculi of the subject eye 211 travels, in the opposite direction, along the same path as the one that the beam has once passed when entering the system 220. Part of the beam is reflected by the beam splitter 206, enters the wavefront sensor 215, and is used for measuring the wavefront of the light beam. A publicly-known Shack-Hartmann wavefront sensor may be used as the wavefront sensor 215.

Part of the reflected/scattered light beam that has passed through the beam splitter 206 is reflected by the beam splitter 204 and guided to a light-intensity sensor 214 through a collimator 212 and an optical fiber 213. The light beam that has entered the light-intensity sensor 214 is converted into an electric signal and processed by an image processing unit 225 into a fundus oculi image.

The wavefront sensor 215 is connected to an adaptive optics controller 216 and transmits the wavefront of the light beam that the wavefront sensor 215 has received to the adaptive optics controller 216. The adaptive optics controller 216 is connected to the deformable mirror 208 and deforms the deformable mirror 208 into the form instructed by the adaptive optics controller 216.

The adaptive optics controller 216 calculates such a mirror shape as to correct the wavefront obtained from the wavefront sensor 215 to an aberration-free wavefront. Then, the adaptive optics controller 216 calculates a voltage to be applied to the comb-drive electrodes, the voltage being required for the deformable mirror 208 to reproduce the mirror shape, and transmits the calculated voltage to the deformable mirror 208. The deformable mirror 208 applies the voltage instructed by the adaptive optics controller 216 between the movable comb-drive electrode and the immovable comb-drive electrode to deform the mirror surface into a predetermined shape.

The wavefront measurement of the wavefront sensor 215, the transmission of the wavefront to the adaptive optics controller 216, and the aberration correction instruction of the adaptive optics controller 216 to the deformable mirror are repeated and feedback controlled so that the wavefront is constantly optimum.

Generally, the size of the visual cells observed by the SLO is of the order of 5 µm. In order for a device to have a resolving power of the order of 5 µm, the remaining wavefront aberration RMS of the deformable mirror has to be 0.025 waves or lower. The use of the adaptive optical system according to the embodiment enables the shape of the deformable mirror to approximate to an ideal shape and accurate correction of aberrations, whereby the remaining wavefront aberration RMS can be 0.025 waves or lower.

As described above, the SLO including the adaptive optical system according to an embodiment of the invention can appropriately correct aberrations that can occur in the subject eye and thus can obtain images with high resolution.

TEST EXAMPLES

To confirm the deformable mirror according to the embodiment of the invention, simulations were conducted on samples 1 to 5 having different combinations of the film thicknesses of the first region and the second region. A commercially available software (manufactured from ANSYS) that can analyze with finite-element method was used in the simulations.

Figure 8:
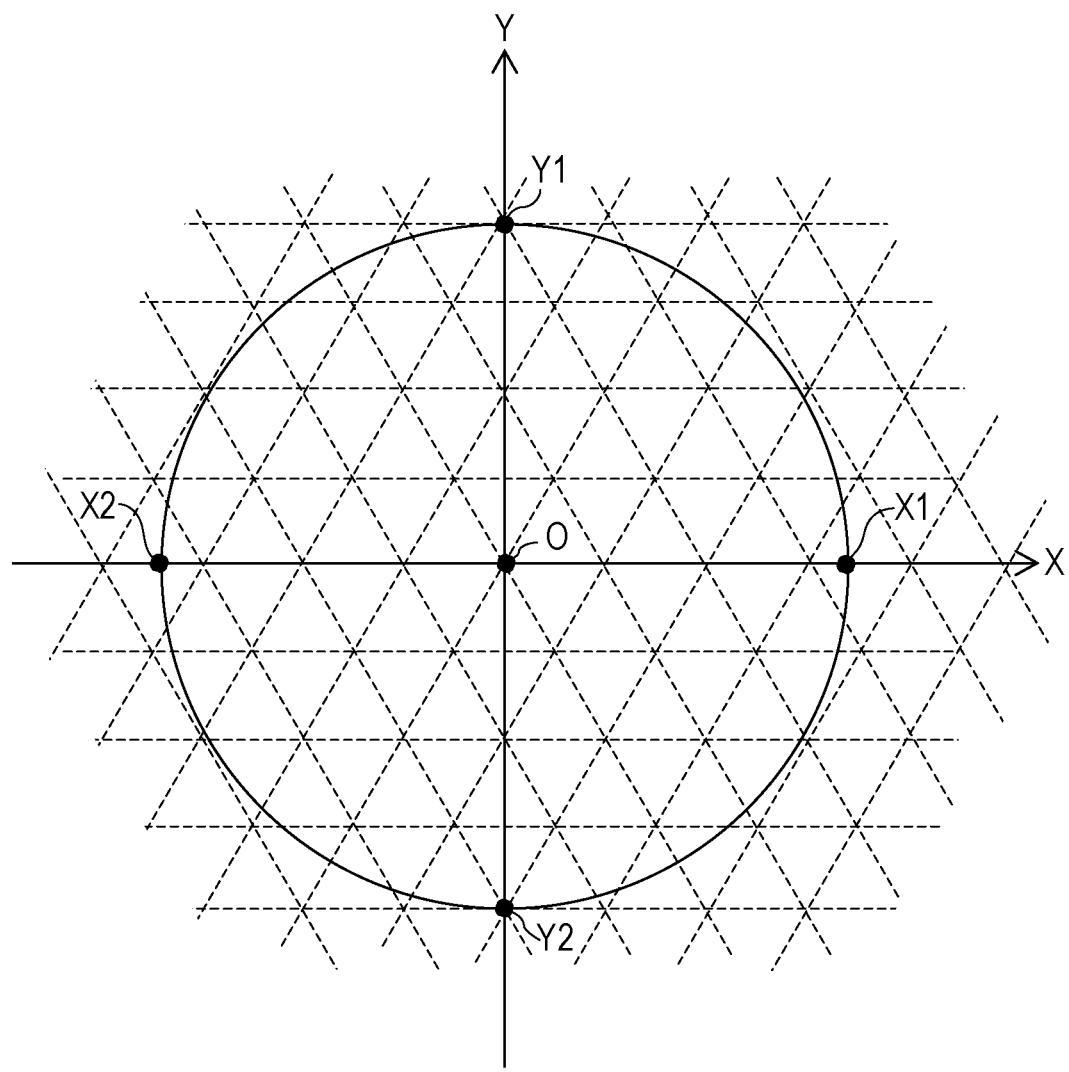
FIG. 8 illustrates an effective diameter range of a deformable mirror used in the simulation and the positions of the coupling portions of the deformable mirror.

The simulation conditions are described as follows. Coupling portions are formed uniformly throughout the deformable mirror, not only in the range of the effective mirror diameter. FIG. 8 illustrates the effective diameter range of the deformable mirror. In FIG. 8, the circle drawn with the solid line indicates the effective mirror diameter. The junctions correspond to the coupling portions.

Deformable mirror diameter: 15 mmφ
Effective mirror diameter: 7.5 mmφ
Mirror substrate: single crystal silicon (Young's modulus of 130,000 and Poisson's ratio of 0.3)
Arrangement of coupling portions: triangular grid
Pitch of coupling portions: 1,082 µm
Coupling portion diameter: 30 µmφ)
Width of first region (thin portion): 30 µm
Ideal shape: Astigma
Amount of displacement from the mirror center O of the effective mirror diameter:
Intersections on X axis (X1 and X2): +3.75 µm
Intersections on Y axis (Y1 and Y2): −3.75 µm

| | mirror substrate thickness of first region | mirror substrate thickness of second region |
|---|---|---|
| Sample 1 (Example 1) | 0.3 µm | 1.2 µm |
| Sample 2 (Comparative Example 1) | 1.2 µm | |
| Sample 3 (Example 2) | 1.2 µm | 5.0 µm |
| Sample 4 (Example 3) | 2.0 µm | |
| Sample 5 (Example 4) | 3.0 µm | |
| Sample 6 (Comparative Example 2) | 5.0 µm | |

FIGS. 9A, 9B, 10A and 10B illustrate the x and y coordinates of each sample resulting from the simulation. In each drawing, the ideal shape is drawn with dotted lines and the positions of the coupling portions are indicated by arrows.

Figure 9A:
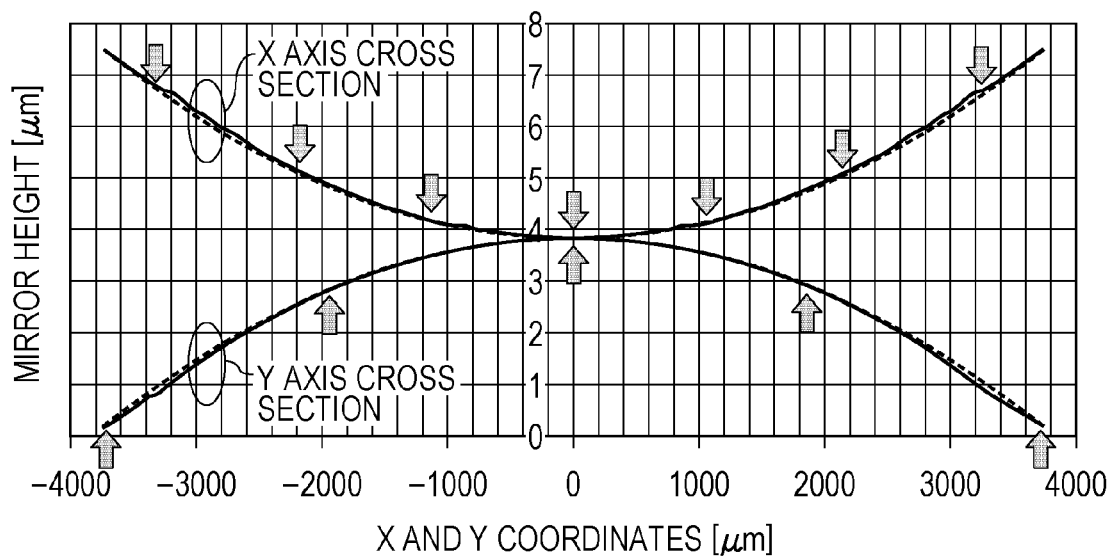
FIGS. 9A and 9B are graphs showing the shapes of deformable mirrors resulting from the simulation, in which the thickness of the mirror substrate in a second region is 1.2 μm.
Figure 9B:
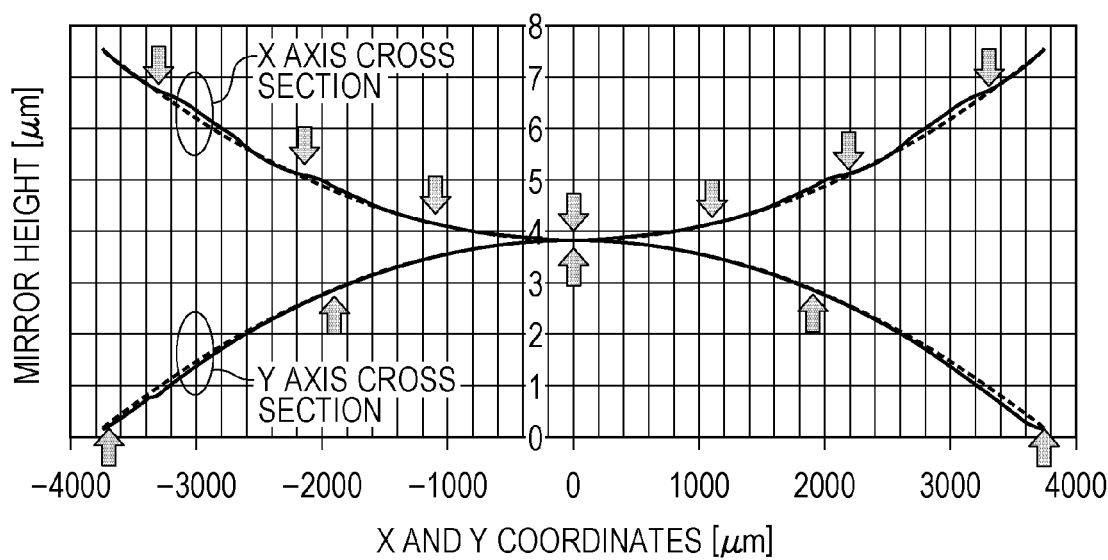
Figure 10A:
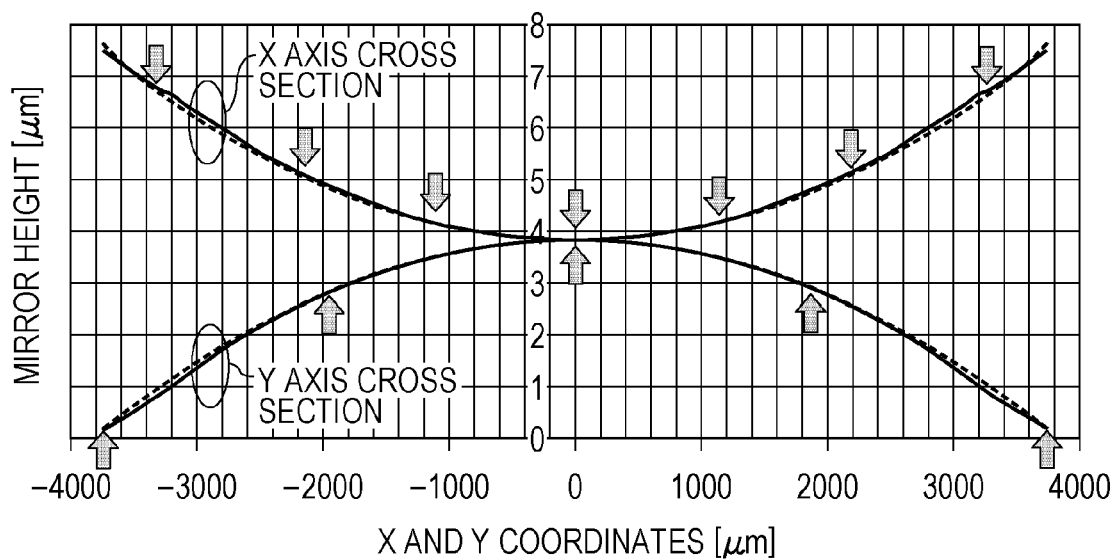
FIGS. 10A and 10B are graphs showing the shapes of deformable mirrors resulting from the simulation, in which the thickness of the mirror substrate in a second region is μm.
Figure 10B:
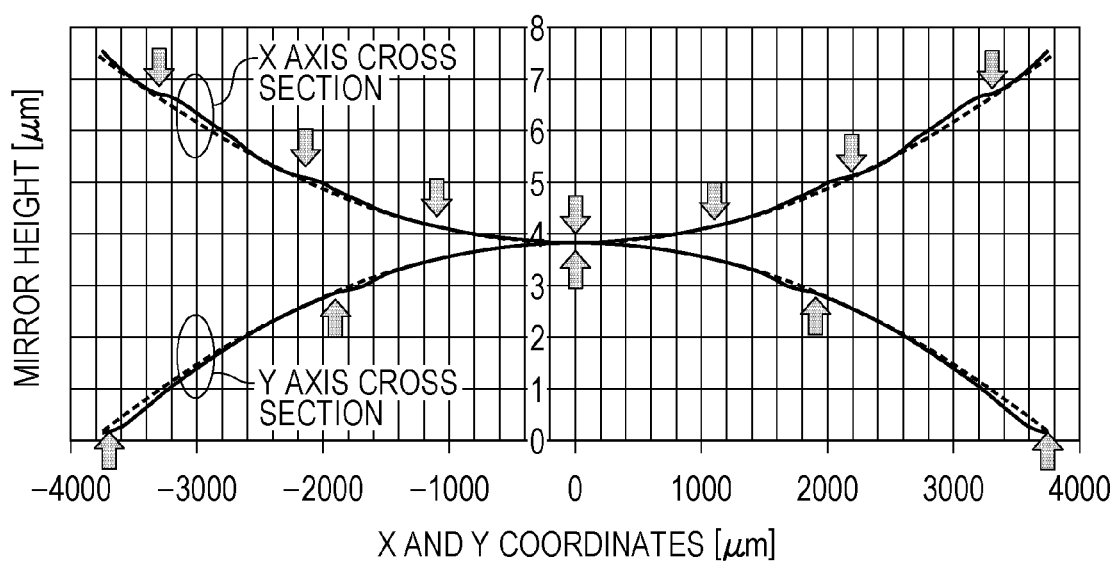

FIGS. 9A and 9B illustrate the simulation results regarding the samples 1 and 2 with the solid lines. FIG. 10A illustrates the simulation results regarding the samples 3 and 5 and FIG. 10B illustrates the simulation result regarding the sample 6. In FIG. 10A, the simulation result regarding the sample 3 is drawn with the solid line and the simulation result regarding the sample 5 is drawn with the dot-and-dash line.

The simulation results illustrated in FIGS. 9A, 9B, 10A, and 10B show that the samples 1, 3, and 5 corresponding to the examples according to the embodiment of the invention can have a mirror surface that deviates from the ideal shape to a lesser extent in the coupling portions than the samples 2 and 6 according to the comparative examples.

Figure 11A:
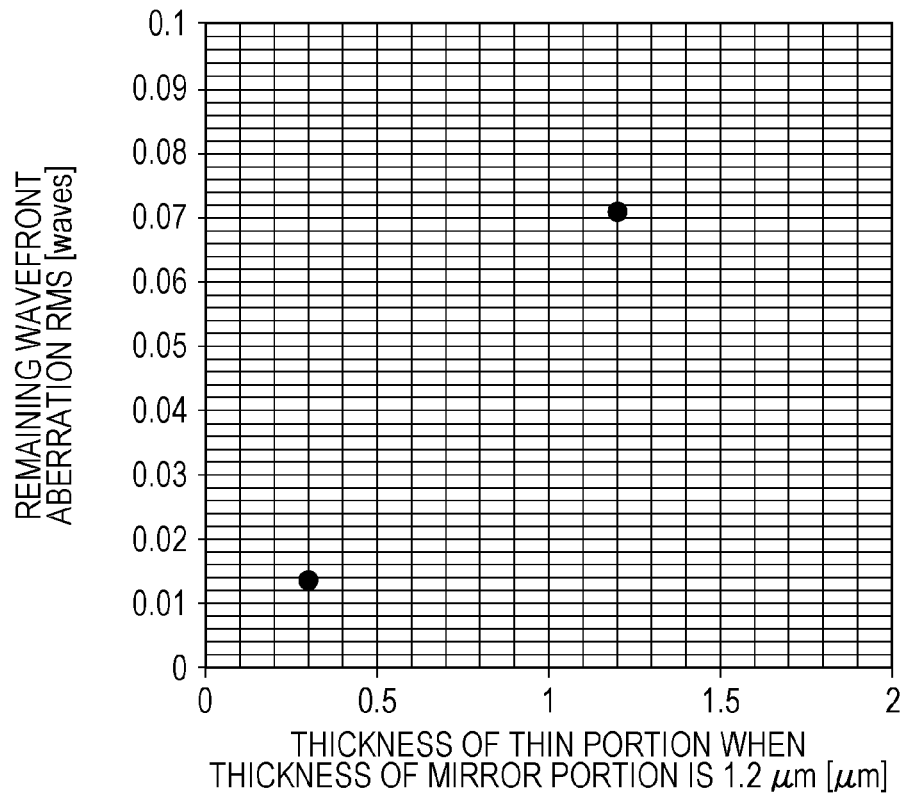
FIGS. 11A and 11B are graphs showing simulated wavefront aberration remaining after the correction of a wavefront aberration correction device including the deformable mirror according to an embodiment of the invention.
Figure 11B:
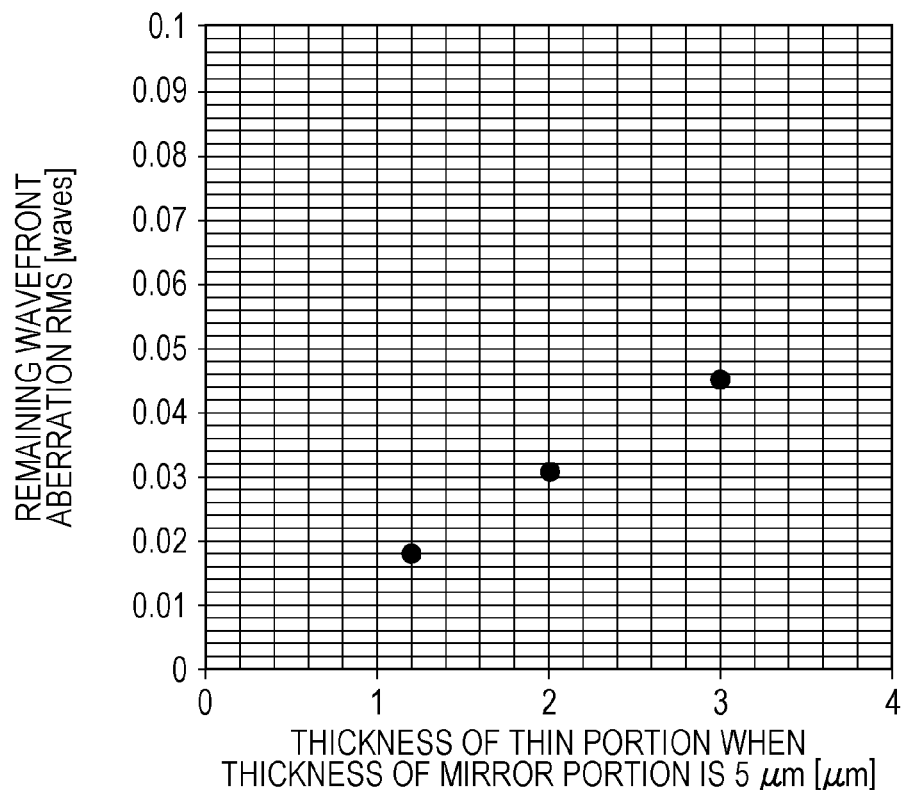

Subsequently, the wavefront aberration in the samples 1 to 5 remaining after the correction of the wavefront aberration correction device including the deformable mirror was calculated using the optical simulation CODE V manufactured from Synopsys. FIG. 11A illustrates the simulation results regarding the samples 1 and 2 and FIG. 11B illustrates the simulation results regarding the samples 3 to 5. FIGS. 11A and 11B show that the remaining aberration can be reduced as the thickness of the mirror substrate in the first region is reduced relative to the thickness of the mirror substrate in the second region.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-029355 filed Feb. 18, 2013 and No. 2014-016379 filed Jan. 31, 2014, which are hereby incorporated by reference herein in their entirety.

What is claimed is:

1. A deformable mirror, comprising:
a mirror substrate having a continuous reflective surface; and
a plurality of actuators connected to the mirror substrate at a plurality of coupling portions,
wherein the mirror substrate has first regions and a second region thicker than the first regions,
wherein the first regions are arranged around the coupling portions,
wherein each of the actuators is connected to the mirror substrate at a different one of the coupling portions, and
wherein the second region is arranged between two coupling portions adjacent to each other.

2. The deformable mirror according to claim 1, wherein each first region has a continuous area or discrete areas arranged so as to surround a corresponding one of the coupling portions.

3. The deformable mirror according to claim 1, wherein the mirror substrate has recesses in the first regions on the surface to which the actuators are connected.

4. The deformable mirror according to claim 1, wherein a thickness of the mirror substrate gradually increases from each first region to the second region.

5. The deformable mirror according to claim 1, wherein the mirror substrate is connected to an immovable portion that fixes the plurality of actuators at a circumferential portion of the mirror substrate.

6. The deformable mirror according to claim 1, wherein in the coupling portion, a post and a pad are interposed between the mirror substrate and the corresponding actuator.

7. The deformable mirror according to claim 1, wherein the actuator includes:
a movable portion connected to the mirror substrate;
a movable comb-drive electrode supported by the movable portion and extending in a direction parallel to the reflective surface of the mirror substrate;
a supporting portion that supports the movable portion; and
an immovable comb-drive electrode supported by the supporting portion, extending in a direction parallel to the reflective surface of the mirror substrate, and disposed so as to interlock with the movable comb-drive electrode.

8. The deformable mirror according to claim 1, wherein the thickness of the mirror substrate at the coupling portion is larger than the thickness in the first region so as to form a protruding portion and the diameter of the protruding portion of the mirror substrate at the coupling portion decreases from a coupling side of the mirror substrate toward a reflective-surface side of the mirror substrate.

9. An apparatus comprising:
a reflective light modulator that corrects wavefront aberration of light entering the system;
an aberration measuring unit that measures wavefront aberration of light entering the system; and
a control unit that controls the reflective light modulator on the basis of results of measurement of the aberration measuring unit,
wherein the reflective light modulator includes the deformable mirror according to claim 1.

10. The deformable mirror according to claim 1, wherein the second region is arranged between the first regions.

11. The deformable mirror according to claim 1, wherein a thickness of the mirror substrate at the coupling portion is the same as a thickness of the first region or a thickness of the second region.

12. A deformable mirror, comprising:
a mirror substrate having a continuous reflective surface; and
a plurality of actuators connected to the mirror substrate at a plurality of coupling portions,
wherein the actuator includes a movable portion being displaced in a direction intersecting with an in-plane direction of the reflective surface,
wherein the mirror substrate has first regions and a second region thicker than the first regions,
wherein the first regions are arranged around the coupling portions, and
wherein the second region is arranged between two coupling portions adjacent to each other.

13. The deformable mirror according to claim 12, wherein a width of the first regions is smaller than a width of the second region between two coupling portions adjacent to each other.

14. The deformable mirror according to claim 12, wherein a width of the coupling portion is smaller than a width of the second region between two coupling portions adjacent to each other.

15. The deformable mirror according to claim 12, wherein the second region is thinner than the movable portion of the actuator in the direction intersecting with the in-plane direction of the reflective surface.

16. The deformable mirror according to claim 12,
wherein a thickness of the mirror substrate increases from each first region to the second region.

17. An apparatus, comprising:
a reflective light modulator that corrects wavefront aberration of light entering the system;
an aberration measuring unit that measures wavefront aberration of light entering the system; and
a control unit that controls the reflective light modulator on the basis of results of measurement of the aberration measuring unit,
wherein the reflective light modulator includes the deformable mirror according to claim 12.

18. A deformable mirror, comprising:
a mirror substrate having a continuous reflective surface; and
a plurality of actuators connected to the mirror substrate at a plurality of coupling portions,
wherein the actuator includes a movable comb-drive electrode and an immovable comb-drive electrode,
wherein the mirror substrate has first regions and a second region thicker than the first regions,
wherein the first regions are arranged around the coupling portions, and
wherein the second region is arranged between two coupling portions adjacent to each other.

19. A deformable mirror, comprising:
a mirror substrate having a continuous reflective surface; and
a plurality of actuators connected to the mirror substrate at a plurality of coupling portions,
wherein the mirror substrate has first regions and a second region thicker than the first regions,
wherein the first regions are arranged around the coupling portions,
wherein the second region is arranged between two coupling portions adjacent to each other, and
wherein a width of the coupling portion is smaller than a width of the second region between two coupling portions adjacent to each other.

20. A deformable mirror, comprising:
a mirror substrate having a continuous reflective surface; and
a plurality of actuators connected to the mirror substrate at a plurality of coupling portions,
wherein the actuator includes a movable portion,
wherein the mirror substrate has first regions and a second region thicker than the first regions,
wherein the first regions are arranged around the coupling portions,
wherein the second region is arranged between two coupling portions adjacent to each other, and
wherein the second region is thinner than the movable portion of the actuator in a movable direction.

21. A deformable mirror, comprising:
a mirror substrate having a continuous reflective surface; and
a plurality of actuators connected to the mirror substrate at a plurality of coupling portions of the mirror substrate,
wherein the mirror substrate has first regions and a second region thicker than the first regions,
the first regions are formed around the coupling portions,
the second region is formed around the first regions,
wherein, for each of the actuators, a respective portion of the reflective surface, the respective coupling portion and a movable portion of the actuator are arranged in this order, and
wherein each of the actuators is arranged to individually displace the respective portion of the reflective surface via the respective coupling portion relative to another portion of the reflective surface different from the respective portion in a direction in which the respective portion of the reflective surface, the respective coupling portion and the movable portion of the actuator are arranged,
the second region is formed between two coupling portions adjacent to each other, and
a thickness of the mirror substrate at the coupling portions is the same as a thickness of the second region.

22. The deformable mirror according to claim 21, wherein each first region has a continuous area or discrete areas formed so as to surround a corresponding one of the coupling portions.

23. The deformable mirror according to claim 21, wherein the mirror substrate has recesses forming the first regions on the surface to which the actuators are connected.

24. The deformable mirror according to claim 21, wherein a thickness of the mirror substrate gradually increases from each first region to the second region.

25. The deformable mirror according to claim 21, wherein the mirror substrate is connected to an immovable portion that fixes actuators of the plurality of actuators at a circumferential portion of the mirror substrate and the mirror substrate also includes one of the first regions on an inner periphery of a coupling portion connected to the immovable portion.

26. The deformable mirror according to claim 21, wherein in each coupling portion, a post and a pad are interposed between the mirror substrate and the corresponding actuator.

27. The deformable mirror according to claim 21, wherein each of the plurality of actuators includes:
a movable portion connected to the mirror substrate; a movable comb-drive electrode supported by the movable portion and extending in a direction parallel to the reflective surface of the mirror substrate; a supporting portion that supports the movable portion; and an immovable comb-drive electrode supported by the supporting portion, extending in a direction parallel to the reflective surface of the mirror substrate, and disposed so as to interlock with the movable comb-drive electrode.

28. The deformable mirror according to claim 21, wherein a thickness of the mirror substrate at the coupling portion is larger than a thickness in the first region so as to form a protruding portion and the diameter of the protruding portion of the mirror substrate at each coupling portion decreases from a coupling side of the mirror substrate toward a reflective-surface side of the mirror substrate.

29. The deformable mirror according to claim 21, wherein each of the actuators is connected to the mirror substrate at a different one of the coupling portions.

30. An adaptive optical system that corrects wavefront aberration, comprising: a reflective light modulator that corrects wavefront aberration of light entering the system; an aberration measuring unit that measures wavefront aberration of light entering the system; and a control unit that controls the reflective light modulator on the basis of results of measurement of the aberration measuring unit, wherein the reflective light modulator includes the deformable Mirror according to claim 21.

31. An ophthalmological device that captures an image of a subject eye, comprising: a reflective light modulator that corrects wavefront aberration of at least one of measurement light and return light; an aberration measuring unit that measures aberration that occurs at the subject eye; and a control unit that controls the reflective light modulator on the basis of results of measurement of the aberration measuring unit, wherein the reflective light modulator includes the deformable mirror according to claim 21.

32. The ophthalmological device according to claim 31, further comprising a light source that emits a laser beam having a wavelength not exceeding 850 nm.

\* \* \* \* \*